Figure 3:
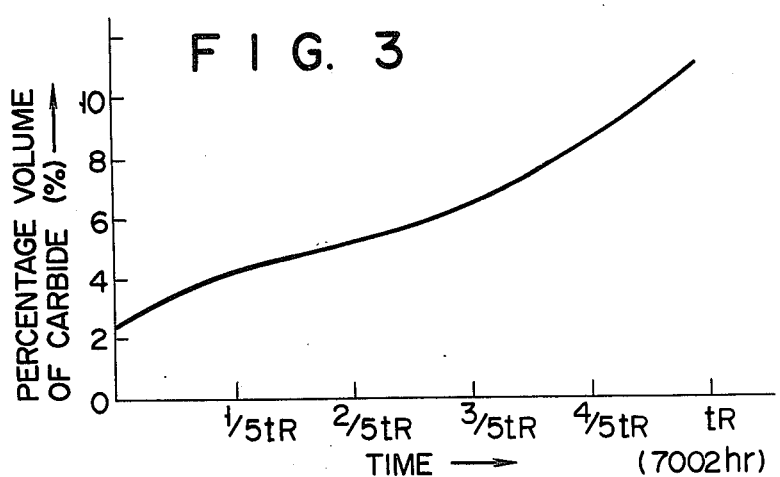

United States Patent [19]

Komatsu et al.

[11] 4,287,417

[45] Sep. 1, 1981

[54] METHOD OF DETERMINING THE DETERIORATION OF HEAT-RESISTANT FERRITIC STEEL PARTS

[75] Inventors: Shuichi Komatsu; Shinichi Nakamura, both of Yokohama; Kazumi Shimotori, Kawasaki; Yoshio Nakayama, Yokohama, all of Japan

[73] Assignee: Tokyo Shibaura Denki Kabushiki Kaisha, Kawasaki, Japan

[21] Appl. No.: 115,884

[22] Filed: Jan. 28, 1980

[30] Foreign Application Priority Data

Jan. 31, 1979 [JP] Japan .................................... 54-9122
Aug. 31, 1979 [JP] Japan ................................ 54-110303

[51] Int. Cl.³ .......................................... G01N 23/00
[52] U.S. Cl. .................................................... 250/307
[58] Field of Search ............... 250/306, 307, 311, 312, 250/320, 321, 358 R

[56] References Cited

U.S. PATENT DOCUMENTS 2,613,326  10/1952  Herzog ................................. 250/307

FOREIGN PATENT DOCUMENTS 52-33587  9/1975  Japan ..................................... 250/307

OTHER PUBLICATIONS

Williams et al., "Effects of Microstructural Instability of the Creep and Fracture Behaviour of Ferric Steels", Material Science & Engineering, vol. 28, pp. 289-295, (1977).
Prnka et al., "Effect of Carbide Repartition on the Creep Rupture Strength of Low Alloy Cr–Mo–V Steels", Arch. Eisenhuttenwes, vol. 44, No. 4, Apr. 1973, p. 321.
"A Rapid Method of Obtaining Electron Microscope Contrast Maps of Various Lattice Defects", Thölen, Phil. Mag., vol. 22, No. 175, Jul. 1970, pp. 175-182, 250-307.

Primary Examiner—Bruce C. Anderson
Attorney, Agent, or Firm—Oblon, Fisher, Spivak, McClelland & Maier

[57] ABSTRACT

A method of determining the degree of deterioration of a heat-resistant ferritic steel part, such as that of Cr-Mo-V steel practically applied in a region of high temperature from at least one of the crystallization factors such as the particle size, interparticle distance and crystallization density of a carbide, particularly $V_4C_3$ crystallized out in said ferritic steel part.

3 Claims, 7 Drawing Figures

F I G. 1
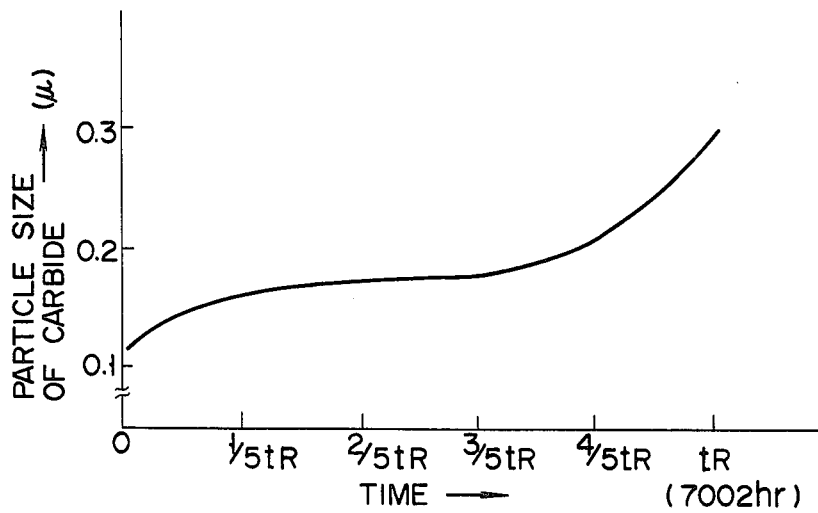
F I G. 2
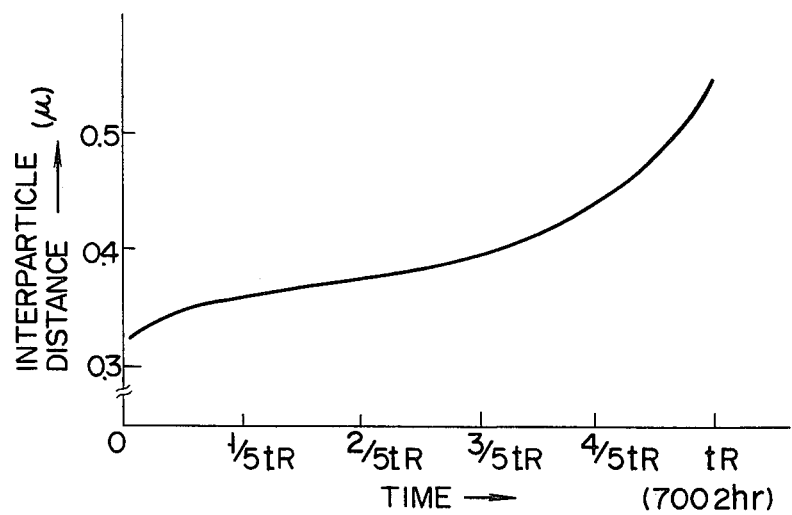

METHOD OF DETERMINING THE DETERIORATION OF HEAT-RESISTANT FERRITIC STEEL PARTS

This invention relates to a method of determining the deterioration with time of heat-resistant ferritic steel parts applied in a high temperature region.

The rotor and blades of a steam turbine are generally formed of heat-resistant ferritic steel. The heat-resistant steel of these steam turbine parts is progressively deteriorated, as the steam turbine is long operated in the high temperature region. This deterioration necessarily leads to a decline in the mechanical strength of said ferritic steel parts, rendering them unadapted for any further application and in some cases resulting in the occurrence of an accident. Particularly where a steam turbine is practically applied to power generation, an accident occurring in the turbine would obstruct a stable power supply. For prevention of such accident, therefore, a periodic examination is made of steam turbine parts such as a rotor and blades to determine the degree of deterioration occurring in the parts from their deformation or any other defects. However, a method of examination followed to date failed to accurately define the degree of deterioration of such heat-resistant steel parts. Therefore, it has been demanded to develop a novel method of accurately judging the deterioration with time of, for example, steam turbine parts made of heat-resistant ferritic steel simply by sampling small portions of these parts.

It is accordingly the object of this invention to provide a method of determining easily and accurately the deterioration with time of heat-resistant ferritic steel parts applied in a high temperature region.

The method of this invention estimates the degree of deterioration of heat-resistant ferritic steel parts long applied in a high temperature region from the crystallization factors of a carbide crystallized out in said steel parts such as the particle size, interparticle distance, and the percentage volume or crystallization density of crystallized carbide particles. Particularly with heat-resistant ferritic steel containing vanadium, for example, steel of the Cr-Mo-V series, the crystallization factors of vanadium carbide $V_4C_3$ well conform to the mechanical strength of the steel. Therefore, the deterioration with time of parts made of the heat-resistant ferritic steel containing vanadium applied in a high temperature region should preferably be determined from said crystallization factors of vanadium carbide.

Accordingly, this invention provides a method of determining the degree of deterioration of heat-resistant ferritic steel parts, which comprises the steps of:

measuring at least one of the crystallization factors of a carbide crystallized out in a heat-resistant ferritic steel part practically applied in a region of high temperature;

obtaining a heating time during which the same type of steel as that of said steel part is to be applied under test-accelerating conditions to produce said at least one crystallization factor from the referential deterioration curves (FIGS. 1 to 6) showing the relationship between the heating time of the sample steel and the crystallization factors of a carbide crystallized out in said sample steel; and calculating a period of time for which the ferritic steel parts have already been put to practical application from the heating time of the steel under test-accelerating conditions, by applying the Larson-Miller parameter $P = T(\log t + c)$ where:

$P$ = a constant defined by a value denoting a crystallization factor,
$T$ = absolute temperature,
$t$ = a period of time, and
$c$ = a constant defined by the material of a ferritic steel part which is preferred to be 20 with respect to heat-resistant ferritic steel.

Figure 4:
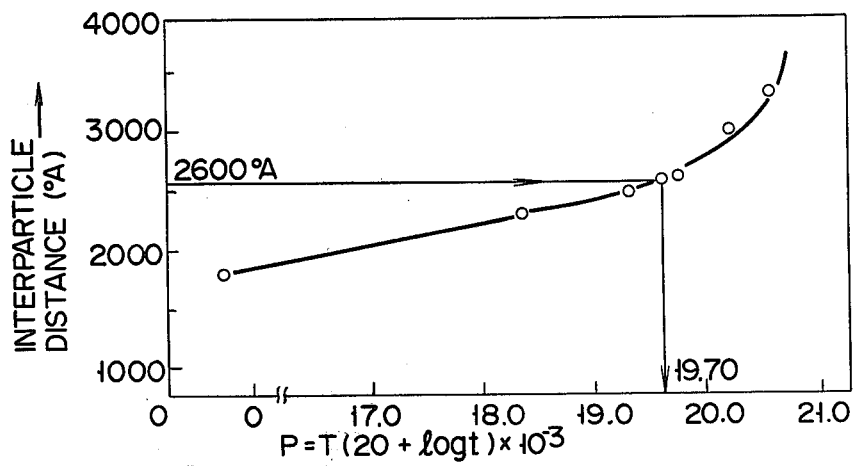
Figure 5:
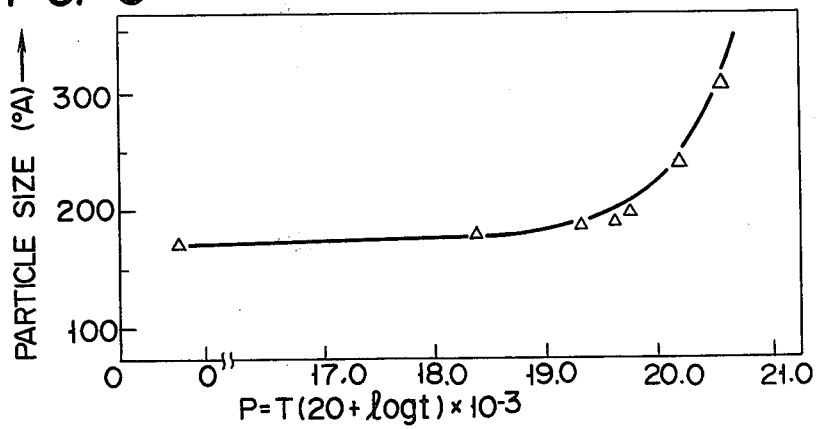
Figure 6:
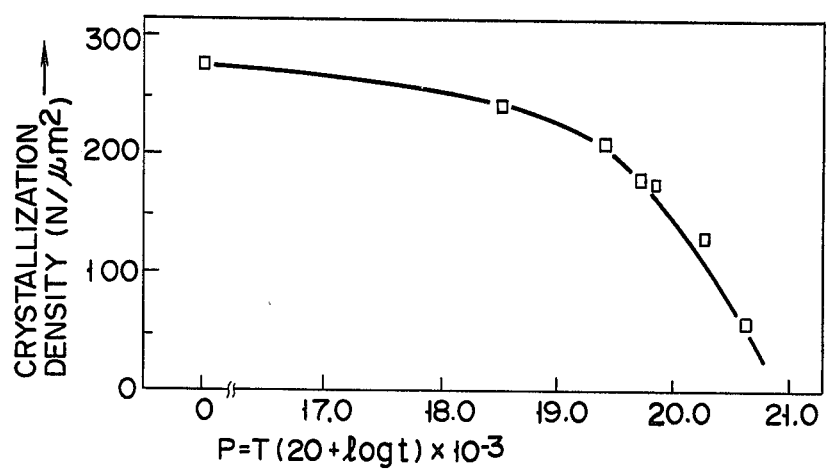

Obviously, the above-mentioned referential deterioration curves may be of the type which shows, as seen from FIGS. 4 to 6, the relationship between the Larson-Miller parameter denoting the functions of temperature and time and the aforesaid crystallization factors of a carbide crystallized out in a ferritic steel part.

Further, if a period of time calculated by the method of this invention during which, for example, turbine parts of ferritic steel are supposed to have actually been put to practical application is subtracted from an already known period of time required for the steel material of said turbine parts to be finally ruptured under the conditions of practical application, then it is possible to estimate the remaining effective life of the steel parts.

Figure 7:
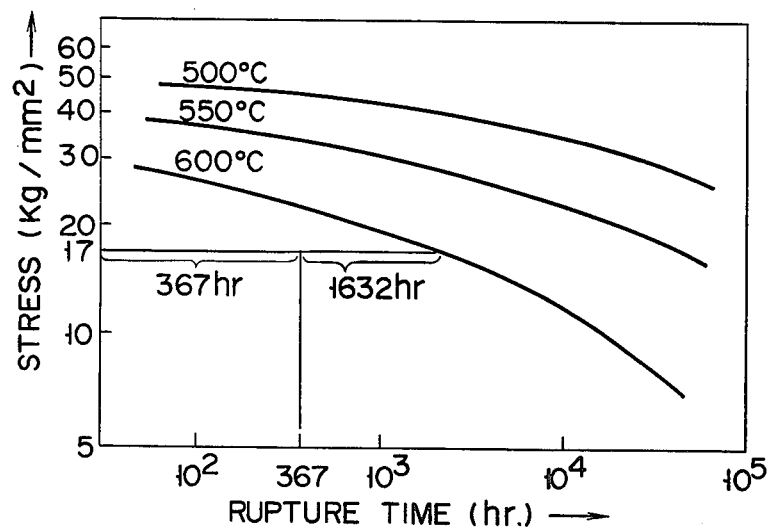

This invention can be more fully understood from the following detailed description when taken in conjunction with the accompanying drawing(s), in which:

FIG. 1 graphically shows the relationship between the period of time during which a sample of Cr-Mo-V steel is subjected to test-accelerating conditions and the particle size of a carbide crystallized out in said sample steel;

FIG. 2 graphically indicates the relationship between the period of time during which a sample of the same type of steel as in FIG. 1 is subjected to the same test-accelerating conditions and the interparticle distance of a carbide crystallized out in said sample steel;

FIG. 3 graphically illustrates the relationship between the period of time during which said sample is subjected to the same test-accelerating conditions and the percentage volume of a carbide crystallized out in said sample steel;

FIG. 4 graphically sets forth the relationship between the Larson-Miller parameter determined by the creep test of the Cr-Mo-V steel carried out under various conditions of temperature and time and the interparticle distance of $V_4C_3$ crystallized out in said Cr-Mo-V steel;

FIG. 5 graphically shows the relationship between the Larson-Miller parameter and the particle size of $V_4C_3$ crystallized out in said Cr-Mo-V steel;

FIG. 6 graphically indicates the relationship between the Larson-Miller parameter and the density of $V_4C_3$ crystallized out in said Cr-Mo-V steel; and FIG. 7 graphically sets forth the relationship between the stresses applied to the Cr-Mo-V steel at temperatures of 500°, 550° and 600° C. and the periods of time required for said Cr-Mo-V steel to be ruptured at said temperatures.

Improvement on the mechanical strength of heat-resistant ferritic steel used as the material of, for example, a rotor of a steam turbine is attempted by causing fine particles of carbides such as $M_3C$, $M_7C_3$ and $M_{23}C_6$ (M is a metal element) to be crystallized out by heat treatment in the matrix of said ferritic steel. Particularly, in the case of vanadium-containing steel, it is tried to elevate the mechanical properties such as creep rupture strength of said steel by chasing fine particles of vanadium carbide $V_4C_3$ to be crystallized out by heat treatment uniformly through the matrix of said steel.

Where, however, the heat-resistant steel is applied in a high temperature region and under great stresses, then the difficulties arise that as time goes on, various carbides including $V_4C_3$ grow larger. The noticeable growth such carbides in heat-resistant steel has been assumed to the related to the deterioration of said steel. To date, however, said relationship has not be quantitatively determined. It has been regarded as difficult to carry out the quantitative analysis of particularly vanadium carbide which is crystallized out in heat-resistant steel in the form of extremely fine particles. The present inventors have closely studied the crystallization behavior of the previously described carbides expressed as $M_3C$, $M_7C_3$, $M_{23}C_6$ and $V_4C_3$, and as a result have discovered that the crystallization factors of these carbides such as the particle size, interparticle distance and percentage volume are closely related to the deterioration of the aforesaid heat-resistant steel, in other words, a period of time for which said steel can be practically applied in a high temperature region, and that said relationship can be properly defined by the Larson-Miller parameter $P = T(\log t + c)$.

It has also been disclosed that particularly fine $V_4C_3$ particles can be let to appear on the screen of an electronic microscope by the dark view field process; and the crystallization factors of said $V_4C_3$ particles determined by the quantitative analysis of the image of said $V_4C_3$ particles on a computer-type image-processing apparatus can be finally defined by the Larson-Miller parameter.

As a result, it has become possible to easily estimate the degree of deterioration of heat-resistant ferritic steel parts by subjecting said steel to a creep test conducted at a higher temperature (accelerated temperature) than that which prevails in the region where the parts are practically applied; determining the relationship between the crystallization factors of a crystallized carbide and the Larson-Miller parameter (that is, the accelerated temperature applied in the creep test and the length of time for which the steel is tested); and utilizing the relationship charts (deterioration curves) with reference to the crystallization factors of a carbide crystallized out in practically applied steam turbine parts of ferritic steel.

There will now be described in greater detail a method embodying this invention for determining the degree of deterioration of heat-resistant ferritic steel parts. A sample of heat-resistant ferritic steel, for example, 1% Cr-1% Mo-0.25% V steel was provided for a creep test. This test was carried out under an accelerated condition of a higher temperature of 600° C. than in practical application and a stress of 10 kg/mm². Measurement was made at the end of each prescribed period of time of the crystallization factors (the particle size, interparticle distance and percentage volume) of a carbide crystallized out in the sample steel by applying an electronic microscope and processing an image produced. As a result, referential deterioration curves (FIGS. 1 to 3) were provided. A rupture time of sample steel was also measured under the above-mentioned test conditions. Referring to FIG. 1, the rupture time (tR) was 7,002 hours. On the other hand, a test piece was sampled from a heat-resistant ferritic steel part put to practical application at a temperature of, for example, 580° C. and under a stress of 10 kg/mm². The crystallization factors of a carbide crystallized out in the above-mentioned test piece was determined by applying an electronic microscope and processing an image produced. A heating time required for said crystallization factors to be produced during the test carried out under the accelerated condition was determined from the referential deterioration curve. Said determined heating time was converted by means of the Larson-Miller parameter into a length of time which would be required for the crystallization factors of a carbide crystallized out in the sample to be produced at a temperature of, for example, 580° C. used in practical application. It was found that the calculated remaining effective life of a practically applied ferritic steel part arrived at by subtracting the length of time obtained by said conversion from the known rupture time of said ferritic steel well coincided with the remaining effective life of a practically applied ferritic steel part.

It is already known that the crystallization factors of carbides such as $M_3C$, $M_7C_3$ and $M_{23}C_6$ can be determined by processing the structural images of said crystallized carbides obtained by the ordinary bright view field process of an electronic microscope. However, a $V_4C_3$ which is crystallized out in a ferritic steel part in the form of extremely fine particles fails to be quantitatively analyzed with high precision. Therefore, a method embodying this invention for determining the deterioration of heat-resistant ferritic steel parts is based on the dark view field process of an electronic microscope. $V_4C_3$ particles precipitated in a given alloy crystal system are arranged in the same direction. Therefore, the images of said crystallized $V_4C_3$ particles by the dark view field process of an electronic microscope always appear in the form of white dots by electron beams diffracted in clear distinction from other forms of carbide. When the structural image of the $V_4C_3$ particles derived from the dark view field process is processed by a computer, then the crystallization factors of the $V_4C_3$ particles can be accurately determined.

The method of this invention can determine the degree of deterioration of heat-resistant ferritic steel parts or estimate their remaining effective life with high precision. As seen from FIGS. 1 to 6, greater changes take place in the crystallization factors such as particle size and interparticle distance of a carbide precipitated in said heat-resistant ferritic steel parts, as they are practically applied for a longer period of time or the Larson-Miller parameter represents a larger value. In other words, as the heat-resistant ferritic steel parts are deteriorated to an extent more approaching the point of rupture, the subsequent application of said parts for any short period of time leads to noticeable variations in their crystallization factors.

This invention will be more fully understood from the following example.

Determination was made as follows of the degree of deterioration of a steam turbine part which was made of ferritic steel containing 1% Cr, 1% Mo and 0.3% V, and whose operation history was unknown. A test piece was sampled from this turbine part. A vanadium carbide $V_4C_3$ crystallized out in the test piece in an extremely fine particle size was observed by the dark view field process of an electronic microscope. The observed image of said crystallized $V_4C_3$ particles was quantitatively analyzed by an image-processing apparatus, showing that the interparticle distance was 2,600 Å. Previously, the same form of steel as mentioned above was examined under test-accelerating conditions to determine the interparticle distance of a carbide $V_4C_3$ crystallized out in said sample steel. A referential deterioration curve of FIG. 4 was obtained. A Larson-Miller parameter corresponding to the aforesaid interparticle distance of 2,600 Å was measured to be 19.70 from the referential deterioration curve of FIG. 4 showing the relationship between the interparticle distance of said $V_4C_3$ and Larson-Miller parameter. Assuming that the aforesaid turbine part made of 1% Cr-1% Mo-0.3% V steel has so far been applied at a temperature of 600° C. and under a stress of 17 kg/mm², then a length of time required for the interparticle distance of 2,600 Å to be produced was calculated to be 368 hours from the Larson-Miller parameter as follows:

$$19.70 = (273 + 600)(\log t + 20).$$

This means that the tested steel part was deteriorated to an extent corresponding to the condition in which said steel part was applied for 368 hours at a temperature of 600° C. and under a stress of 17 kg/mm².

A creep rupture test was made under various conditions on 1% Cr-1% Mo-0.3% V steel. FIG. 7 shows the relationship between the stress and rupture time determined at temperatures of 500°, 550° and 600° C. The rupture time of the steel applied under a stress of 17 kg/mm² was determined to be 2,000 hours from the curve of FIG. 7 representing a temperature of 600° C. Accordingly, the remaining effective life of the steel part which was applied at a temperature of 600° C. and under a stress of 17 kg/mm² was calculated to be $2,000 - 368 = 1,632$. Where the steel part as mentioned above was further applied under the above-mentioned conditions, then the steel part was ruptured in 1,569 hours, showing good coincidence with the remaining effective life of said steel part determined by the method of this invention. With the foregoing embodiment, determination was made of the degree of deterioration and remaining effective life of a turbine steel part from the interparticle distance of $V_4C_3$ crystallized out in said steel part. Substantially the same results were obtained with respect to the particle size of crystallized $V_4C_3$ (FIG. 5) and the density of said crystallized $V_4C_3$.

What we claim is:

1. A method of determining the degree of deterioration of a Cr-Mo-V ferritic steel part applied in a region of high temperature which comprises the steps of:
    measuring the value of at least one of the crystallization factors of vanadium carbide, $V_4C_3$, crystallized out in the Cr-Mo-V ferritic steel part applied in a region of high temperature, wherein said crystallization factors of vanadium carbide are particle size, interparticle distance, percentage volume or crystallization density, and wherein said crystallization factors are measured from the structural image of said crystallized $V_4C_3$ produced by the dark view field process of an electronic microscope;
    applying a previously obtained referential deterioration curve showing the relationship between the length of time for which the Cr-Mo-V steel is applied under test-accelerating conditions and said at elast one of the crystallization factors of vanadium carbide to determine the length of time under test-accelerating conditions necessary to produce the measured value of said at least one crystallization factor of vanadium carbide; and
    calculating the length of time for the steel part to be used under practical operating conditions from the length of time for which the steel is applied under test accelerating conditions to achieve the value shown by said at least one crystallization factor by applying the Larson-Miller parameter
    $P = T (\log t + 20)$
    wherein
    $P$ = a constant,
    $T$ = absolute temperature, and
    $t$ = time.

2. A method of determining the degree of deterioration of a Cr-Mo-V ferritic steel part applied in a region of high temperature which comprises the steps of:
    measuring the value of at least one of the crystallization factors of vanadium carbide, $V_4C_3$, crystallized out in the Cr-Mo-V ferritic steel part applied in a region of high temperature, wherein said crystallization factors of vanadium carbide are particle size, interparticle distance, percentage volume or crystallization density, and wherein said crystallization factors are measured from the structural image of said crystallized $V_4C_3$ produced by the dark view field process of an electronic microscope; and
    applying a previously obtained referntial deterioration curve showing the relationship between the Larson-Miller parameter
    $P = T (\log t + 20)$
    wherein
    $P$ = a constant,
    $T$ = absolute temperature, and
    $t$ = time
    and said at least one of the crystallization factors of vandium carbide to determine the length of time newcessary to produce the measured value of said at least one crystallization factor of vanadium carbide.

3. The method according to claim 1 or 2, wherein the remaining effective life of the Cr-Mo-V ferritic steel part is estimated by subtracting the calculated period of time, necessary to produce the measured value of said at least one crystallization factor, from the previously known rupture time of said ferritic steel.

* * * * *